United States Patent [19]

Becker et al.

[11] Patent Number: 5,187,066
[45] Date of Patent: Feb. 16, 1993

[54] METHODS FOR DETECTING AMPHIPHILIC ANTIGENS

[75] Inventors: Martin Becker; Nurith Kurn, both of Palo Alto; Yen P. Liu, Cupertino; Rajesh D. Patel, Fremont; Thomas M. Houts, Mountain View; John D. Olson, Sunnyvale, all of Calif.

[73] Assignee: Syntex (U.S.A.) Inc., Palo Alto, Calif.

[21] Appl. No.: 479,930

[22] Filed: Feb. 14, 1990

[51] Int. Cl.$^5$ .................... C12Q 1/00; G01N 33/545
[52] U.S. Cl. ........................ 435/7.36; 435/4; 435/7.32; 435/7.7; 435/7.9; 435/30; 435/34; 436/524; 436/527; 436/528; 436/531
[58] Field of Search ............... 435/7.36, 7.32, 4, 30, 435/34, 810, 7.7, 7.94, 7.9; 436/511, 518, 524, 527, 528, 530, 531, 805, 807, 808, 811; 422/57, 58, 61

[56] References Cited

U.S. PATENT DOCUMENTS

| | | | |
|---|---|---|---|
| 3,944,391 | 3/1976 | Harris et al. | 23/230 B |
| 3,959,128 | 5/1976 | Harris et al. | 210/24 |
| 4,497,899 | 2/1985 | Armstrong et al. | 436/510 |
| 4,497,900 | 2/1985 | Abram et al. | 436/511 |
| 4,663,291 | 5/1987 | Rose | 435/7.36 |
| 4,683,196 | 7/1987 | McLaughlin | 435/7.36 |
| 4,721,730 | 1/1988 | Furuyoshi et al. | 436/532 |
| 4,808,314 | 2/1989 | Karplus et al. | 210/649 |
| 4,906,567 | 3/1990 | Connelly | 435/7 |
| 4,959,303 | 9/1990 | Milburn et al. | 436/541 |
| 4,990,442 | 2/1991 | Del Campo | 436/518 |

FOREIGN PATENT DOCUMENTS

303515  2/1989  European Pat. Off.
WO89/00695  1/1989  PCT Int'l Appl.

OTHER PUBLICATIONS

Scott, et al.; VOX SANG.; vol. 52: pp. 272–280 (1987).

Primary Examiner—David Saunders
Assistant Examiner—Christopher L. Chin
Attorney, Agent, or Firm—Shelley G. Precivale; Carol J. Roth

[57] ABSTRACT

This invention is to a method for detecting an amphiphilic antigen in a biological sample suspected of containing the amphiphilic antigen, which method comprises providing in combination a hydrophilic solid support modified to have a hydrophobic surface and an assay medium suspected of containing an amphiphilic antigen, incubating the combination under conditions sufficient for the amphiphilic antigen to bind to the hydrophobic surface, and determining the presence or amount of the amphiphilic antigen bound to the hydrophobic surface.

41 Claims, No Drawings

METHODS FOR DETECTING AMPHIPHILIC ANTIGENS

BACKGROUND OF THE INVENTION

1. Field of the Invention

This invention relates to a method for detecting an amphiphilic antigen in a biological sample suspected of containing the amphiphilic antigen. The invention has particular application to detecting the presence of gram-negative bacteria in a clinical specimen.

Numerous techniques are known for detecting the presence of antigens in a sample, such as a biological fluid, i.e., blood, urine, cell cultures. Many of the these techniques involve cell culture procedures, which are relatively long and complicated, and which give results that are greatly dependent on the skill of the technician. Other techniques, such as electrophoresis, require complicated and/or costly instruments that are not readily available.

Many of the detection techniques involve immunoassays. Some of these techniques involve detecting antibodies to the antigen of interest. Such indirect techniques tend to be inaccurate because antibodies often remain in the human body after the disease has been cured. Therefore, it is preferable to assay for antigens rather than antibodies. Immunoassay techniques for the detection of the presence or amount of antigen in a biological fluid often involve enzyme immunoassays such as the enzyme linked immunosorbent assay, generally referred to as ELISA. Such assays typically involve detecting the antigen of interest by coating the antigen on a bare solid surface or on a surface that has been pre-coated, for example, with a protein which is usually an antibody to the antigen. The surface is then washed to remove unbound antigen. Thereafter, the antigen on the surface is contacted with an antibody for the antigen that is labeled or is capable of being labeled. The surface is again washed and the antibody that has become bound to the surface of the support is detected by detecting the label.

The number of steps required in the above procedure adds significant time and manipulation to the assay. There is, therefore, a need for a method for detecting antigens, especially antigens from gram-negative bacteria, that is more rapid, reliable and cost effective than tests now known or available. It is likewise important that such a test require less manipulation than presently available tests.

2. Related Disclosures

European Published Patent Application No. 0 303 515 discloses a method for assaying an amphipathic analyte, such as a lipoprotein or a lipopolysaccharide, wherein the lipophilic ends of the analytes are bound to a substantially homogeneous lipophilic surface of a solid substrate. Presence of the bound analyte is then determined by conventional methods.

A novel process for removing endotoxin from biological fluids and for removing or reducing the level of endotoxin from the blood of animals is disclosed in U.S. Pat. No. 3,959,128. The process disclosed involves the use of certain non-ionogenic hydrophobic synthetic plastic polymers that are capable of adsorbing endotoxin from biological fluids when placed in intimate contact therewith.

An in vitro process for detecting the presence of endotoxin in a biological fluid wherein the amebocyte lysate from the hemolymph of the horseshoe crab, *Limulus polyphemus*, is contacted with and incubated in the presence of a synthetic plastic polymer capable of adsorbing endotoxin which has previously been contacted with the biological fluid is disclosed in U.S. Pat. No. 3,944,391.

A method for determining *Chlamydia trachomatis* antigen in a clinical specimen is disclosed in U.S. Pat. No. 4,497,899. The method disclosed involves lysing Chlamydia cells in the specimen to release the antigen; coating a bare solid support with the cell lysate; separating the coated support from the specimen; treating the separated support with antibody to form an antigen-chlamydia antibody complex on the support; separating the complex from unbound antibody; treating the bound complex with labeled antiglobulin to form an antigen-antibody-labeled antiglobulin complex on the support; separating the latter complex from unbound labeled antiglobulin; and determining bound labeled antiglobulin as a measure of antigen in the specimen. U.S. Pat. No. 4,497,900 discloses a method for determining *Neisseria gonorrhoeae* analogous to that in U.S. Pat. No. 4,497,899.

Endotoxin-polymyxin B complexes are disclosed in *Vox Sang.* 1987, Vol. 52, pages 272-280, as being useful in an improved ELISA for IgG antibodies to gram-negative endotoxin core glycolipids in sera from blood donors.

SUMMARY OF THE INVENTION

The method of the present invention is directed to the detection of an amphiphilic antigen in a biological sample suspected of containing an amphiphilic antigen. The method involves providing in combination a hydrophilic solid support modified to have a hydrophobic surface and an assay medium suspected of containing an amphiphilic antigen. The combination is then incubated under conditions sufficient for the amphiphilic antigen to bind to the hydrophobic surface. A determination is then made as to the presence or amount of the amphiphilic antigen bound to the surface as an indication of the presence or amount of amphiphilic antigen in the biological sample.

The method of the present invention has particular application in the detection of the presence or amount of antigens from gram-negative bacteria in a biological sample. Of special interest is the detection of antigens from *Chlamydia trachomatis*, *Chlamydia psittaci*, *Neisseria gonorrhoeae* and *Treponema pallidium*. In this manner gram-negative bacterial infections in patients can be detected.

DETAILED DESCRIPTION OF THE INVENTION

Definitions

As used in this specification and appended claims, unless specified to the contrary, the following terms have the meaning indicated:

The term "amphiphilic antigen" refers to a compound or composition to be detected in the method of the invention. Such compounds or compositions contain both a hydrophobic group and a hydrophilic group. The amphiphilic antigen can be monoepitopic or polyepitopic. The hydrophobic group of the amphiphilic antigen is capable of binding to the hydrophobic surface of the solid support of the invention. In addition, the amphiphilic antigen is capable of binding specifically to an antibody and will normally be soluble or can be caused to be soluble in the assay medium. Examples of such amphiphilic antigens are the lipopolysaccharide antigens, i.e., endotoxins, and the lipoprotein antigens that are present in the outer layer of the cell membranes of gram-negative bacteria, for example, *Chlamydia trachomatis*, *Chlamydia psittaci*, *Neisseria gonorrhea* and *Escherichia coli*.

The term "gram-negative bacteria" includes, but is not limited to, *Chlamydia trachomatis*, *Chlamydia psittaci*, *E. coli*, *Pseudonoms fluorescers*, *Azotobacter vinelandii*, *Proteus vulgaris*, Hydrogenomanas sp., *Aerobacter aerogenes*, *Nisseria gonorrhoeae*, *Treponema pallidum*, *Serratia marcescens*, *Achromobacter fischer*, *Bacillus subtilis*, *Bacillus megaterium*, *Sarcina lutea*, *Micrococcus pyogenes*, *Lactobacillus casei*, *Torulopsis utilis* and *Streptomyces griseus*, Shigella, Campylobacter, Salmonella, Legionella, *Hemophillus influenza*, and so forth.

The term "biological sample" refers to a liquid such as a body fluid or semi-solid material obtained from the body of a mammalian subject. The liquid material may be sterile or nonsterile and usually contains cells. The liquid material may be employed without further treatment or the liquid material may be treated to remove cells, debris, and the like. Exemplary of body fluids are whole blood, urine, lymphatic fluid, serum, plasma, saliva, sputum, semen, vaginal fluids and secretions, and cerebral spinal fluid. Body fluids may be removed from the subject, for example, by means of a syringe or needle or by natural expulsion.

The term "assay medium" refers to the medium in which the method of the invention is performed. The assay medium is comprised of the various aqueous solutions necessary to perform the method of the invention. These aqueous solutions include, but are not limited to, solutions containing biological samples suspected of containing an amphiphilic antigen, solutions containing solubilizing agents, solubilization solutions suspected of containing an amphiphilic antigen, solutions containing the appropriate antibodies for the amphiphilic antigen, solutions containing the appropriate binding partners for the antibodies and other ancilliary solutions, for example, solutions used for stabilizing the assay medium and components of the assay, solutions containing additional detergents or surfactants, particularly anionic surfactants, solutions containing binding enhancers, for example, polyalkylene glycols, and solutions containing additional proteins, for example, bovine serum albumin.

The term "antibody" refers to an immunoglobulin which specifically binds to and is thereby defined as complementary with a particular spatial and polar organization of another molecule, in particular, an amphiphilic antigen of the invention. The antibody can be monoclonal or polyclonal and can be prepared by techniques that are well known in the art such as immunization of a host and collection of sera (polyclonal) or by preparing continuous hybrid cell lines and collecting the secreted protein (monoclonal). Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like.

The term "binding partner" refers to a compound or composition recognizing a particular spatial or polar organization of the antibody, e.g., epitopic or determinant site, or a ligand bound to the antibody. Illustrative binding partners include naturally occurring receptors, e.g., specific immunoglobulins, rheumatoid factor antibodies, lectins, protein A, complement component Clq, avidin, and the like.

The term "immune complex" refers to a complex formed between an antibody and its cognate antigen as a result of the binding affinity of the antibody for the antigen, or between a binding partner and its cognate antibody as a result of the binding affinity of the binding partner for the antibody.

The term "label" refers to a label molecule that is covalently or non-covalently bonded to an antigen, an antibody, or to a binding partner. The label is a member of a signal producing system used for the determination of the presence or amount of amphiphilic antigen such as that bound to the hydrophobic surface of the solid support of the method of the invention. Such a signal producing system includes a signal producing means. The label may be isotopic or nonisotopic, preferably nonisotopic. By way of example and not limitation, the label can be a catalyst such as an enzyme, a co-enzyme, a chromogen such as a fluorescer, dye or chemiluminescer, a radioactive substance, and so forth.

The phrase "signal producing means" refers to a means capable of interacting with the label to produce a detectible signal. Such means include, for example, electromagnetic radiation, heat, chemical reagents, and the like. Where chemical reagents are employed, some of the chemical reagents can be included as part of a developer solution. The chemical reagents can include substrates, coenzymes, enhancers, second enzymes, activators, cofactors, inhibitors, scavengers, metal ions, specific binding substances required for binding of signal generating substances, and the like. Some of the chemical reagents such as coenzymes, substances that react with enzymic products, other enzymes and catalysts, and the like can be bound to other molecules or to a support.

The phrase "signal producing system" refers to a system that may have one or more components, at least one component being a label. The signal producing system generates a signal that relates to the presence or amount of amphiphilic antigen in a sample. The signal producing system includes all of the reagents required to produce a measurable signal. When the label is not conjugated, i.e., bound to the antibody, the label is normally bound to a binding partner for the antibody. Other components of the signal producing system can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, preferably by measurement of electromagnetic radiation. For the most part, the signal producing system will involve a chromophoric substrate and enzyme, where chromophoric substrates are enzymatically converted to dyes which absorb light in the ultraviolet or visible region, phosphors, fluorescers or chemiluminescers.

The signal-producing system can include a catalyst, usually an enzyme, and a substrate and may include two or more catalysts and a plurality of substrates, and may include a combination of enzymes, where the substrate of one enzyme is the product of the other enzyme. The operation of the signal producing system is to produce a product which provides a detectable signal related to the presence or amount of amphiphilic antigen in the sample.

A large number of enzymes and coenzymes useful in a signal producing system are indicated in U.S. Pat. No. 4,275,149, columns 19 to 23, and U.S. Pat. No. 4,318,980, columns 10 to 14, which disclosures are incorporated herein by reference. A number of enzyme combinations are set forth in U.S. Pat. No. 4,275,149, columns 23 to 28, which combinations can find use in the subject invention. This disclosure is incorporated herein by reference.

Of particular interest are enzymes which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horseradish peroxidase, lactoperoxidase, or microperoxidase. These and other enzymes, such as hydrolases, transferases, and oxidoreductases, preferably hydrolases such as alkaline phosphatase and β-galactosidase, may also find use when a single enzyme is used as a label. Alternatively, luciferases may be used such as firefly luciferase and bacterial luciferase.

Illustrative coenzymes which find use include NAD[H]; NADP[H], pyridoxal phosphate; FAD[H]; FMN[H], etc., usually coenzymes involving cycling reactions, see particularly U.S. Pat. No. 4,318,980.

The product of the enzyme reaction will usually be a dye or fluorescer. A large number of illustrative fluorescers are indicated in U.S. Pat. No. 4,275,149, columns 30 and 31, which disclosure is incorporated herein by reference.

The term "solid support" refers to a hydrophilic, porous or non-porous water insoluble material. The surface of the solid support may be neutral or charged in nature and must be capable of being rendered hydrophobic by treatment with a hydrophobic reagent. The solid support may be composed of inorganic powders such as silica, magnesium sulfate, and alumina; natural polymeric materials, particularly cellulosic materials and materials derived from cellulose, such as fiber-containing papers, e.g., filter paper, chromatographic paper, etc.; synthetic or modified naturally occurring polymers, such as nitrocellulose, cellulose acetate, polyacrylamide, cross linked dextran, agarose; vitreous materials such as glass, quartz, ceramics, silicon nitride; or plastics that are intrinsically hydrophilic or have been rendered hydrophilic by the presence of hydrophilic functional groups, such as polyacrylate, polyethylene, polypropylene, polystyrene, polyvinyl chloride which may be modified with hydrophilic functional groups such as carboxyl, amino, carboxamido, phosphonate, sulfonate or hydroxyl, for example, sulfonated-polystyrene or carboxylated-polystyrene, etc.; either used by themselves or in conjunction with a structural support composed of other materials, such as glass, ceramics, metals, plastics and the like. The solid support may assume a variety of shapes and forms and may have varied dimensions, depending on the manner of use and measurement. Illustrative solid supports may be in the shape and form of plates, tubes, dipsticks, beads, spheres, strips, pads, or discs, and the like. The solid support will be free of proteins that specifically bind the amphiphilic antigen of the invention or its antibody and will frequently be free of any protein or other specific binding substances.

The term "solubilizing agent" refers to a detergent used to solubilize an amphiphilic antigen contained within the assay medium of the invention. The solubilizing agent can be anionic, cationic, nonionic, or amphoteric. Anionic solubilizing agents include, by way of example and not limitation, alkyl-, alkylether-, dialkyl esters-, alkylaryl-, and alpha olefin-sulfates, sulfonic acids, sulfonates, sulfosuccinates, and sulfosuccinic acids, thialkyl sulfates, alkyl naphthalene sulfonates, phosphonates, phosphate esters, free acid of complex organic phosphate esters, aliphatic hydroxylated phosphate esters, sulfated fatty acid esters, sulfated oils such an castor, sperm, soya bean, glycerol trioleate, neatsfoot, tallow, and oleic acid, n-fatty acid acyl glutamates such as n-lauroyl, n-cocoyl, n-hydrogenated tallowyl, n-mixed fatty acid acyl, carboxylated polyelectrolytes, disproportionated resins, and so forth. Exemplary of cationic solubilizing agents are alkyl quarternary ammonium chlorides such as dialkyl or trimethyl alkyl, e.g., trimethyl soya, dimethyl dehydrogenated tallow, trimethyl cetyl, and trimethyl coco. Exemplary of nonionic solubilizing agents are Triton X 100, Tween 20, alkylglucosides, and so forth. Exemplary of amphoteric solubilizing agents are fatty acid esters of betaine and the like.

The term "alkyl" refers to an aliphatic hydrocarbon chain of 4 to 20 carbons in length unless defined otherwise.

The term "thialkyl" refers to an aliphatic hydrocarbon chain of 4 to 20 carbons in length wherein at least one carbon in the chain is replaced by a sulfur atom.

The term "hydrophobic surface" refers to a surface of a normally hydrophilic solid support of the invention which has been modified to be non-polar and hydrophobic in nature. The hydrophobic surface results from the modification of the hydrophilic solid support by treatment with a hydrophobic reagent.

The term "hydrophobic reagent" refers to a compound or composition that, upon treatment with a hydrophilic solid support of the invention, is capable of generating a hydrophobic surface covalently or noncolavently bound to the hydrophilic solid support. Exemplary of hydrophobic reagents are antibacterial polypeptides having one or more fatty acid side chains of 4 to 12 carbon atoms, siliconizing agents of 1 to 20 carbon atoms, alkylation agents of 4 to 20 carbon atoms, and acylation agents of 4 to 20 carbon atoms.

Examples of antibacterial polypeptides as hydrophobic reagents include, but are not limited to, polymyxin B and protein conjugates thereof. Polymyxin B is a small cyclic cationic polypeptide with a fatty acid side chain which is known to bind to lipopolysaccharide antigens of gram-negative bacteria. Upon treatment with a hydrophilic solid support of the invention polymyxin B generates a hydrophobic surface on the solid support by the presence of its fatty acid side chains. In a similar manner, protein-polymyxin B conjugates, for example, horseradish peroxidase-polymyxin B conjugate and glucose oxidase-polymyxin B conjugate, generate a hydrophobic surface on the hydrophilic solid support of the invention.

Examples of siliconizing agents as hydrophobic reagents include, but are not limited to, alkylsilanes, alkoxysilanes, alkylhalosilanes, and alkyldisilazanes. Alkylsilanes of 1 to 10 carbon atoms are commercially available in organic solvents, for example, Sigmacote ®

(Sigma Chemical Co.) or in dilute aqueous solutions, for example, Aqua-sil (Pierce Chemical Co.), and Silane A-174 (EM Science). Alkoxysilanes of 4 to 20 carbon atoms are commercially available, for example, octyltriethoxysilane (Lancaster). Alkylhalosilanes of 2 to 20 carbons are commercially available, for example, octyltrichlorosilane and dichlorodimethylsilane. Alkyldisilazanes of 6 to 18 carbon atoms are commercially available, for example, hexamethyldisilazane. Upon treatment with a hydrophilic solid support of the invention siliconizing agents generate a hydrophobic surface on the hydrophilic solid support by the presence of their respective alkyl groups.

Examples of alkylation agents as hydrophobic reagents include, but are not limited to, alkyl alcohols of 4 to 20 carbon atoms, alkyl halides of 4 to 20 carbon atoms, alkylsulfonates of 4 to 20 carbon atoms, and alkylamines of 4 to 20 carbon atoms such as octylamine and octadecylamine, all of which are commercially available. Upon treatment with a hydrophilic solid support of the invention alkylation agents generate a hydrophobic surface on the hydrophilic solid support by the presence of their respective alkyl groups.

Examples of acylation agents as hydrophobic reagents include, but are not limited to, fatty acids and their corresponding esters and halides, alkyl sulfonyl halides, alkylisocyanates, and the like. Upon treatment with a hydrophilic solid support of the invention acylation agents generate a hydrophobic surface on the hydrophobic surface on the hydrophilic solid support by the presence of their respective alkyl groups.

SPECIFIC EMBODIMENTS OF THE INVENTION

As mentioned in the Summary of the Invention above, the present invention is directed to a method of detecting an amphiphilic antigen in a biological sample suspected of containing an amphiphilic antigen. The method involves providing in combination a hydrophilic solid support modified to have a hydrophobic surface and an assay medium suspected of containing an amphiphilic antigen. The combination is incubated under conditions sufficient for the amphiphilic antigen to bind to the hydrophobic surface. The presence or amount of amphiphilic antigen bound to the hydrophobic surface is then determined.

In the method of the invention, a biological sample suspected of containing an amphiphilic antigen is first treated with a solubilization solution containing a solubilizing agent in order to solubilize any amphiphilic antigen that might be present in the biological sample. By way of example, but not of limitation, the biological sample may be collected on a collection device such as a swab from the body of a mammalian subject and then inserted into a vial, for example a test tube, containing a solubilization solution for a time sufficient to solubilize any amphiphilic antigen present in the biological sample. The solubilization solution may then be used directly in the assay medium of the invention, may be diluted to reduce the concentration of the solubilizing agent prior to being used in the assay medium, or may be used as the assay medium.

In the method of the invention, hydrophilic solid supports modified to have hydrophobic surfaces are contacted with an assay medium suspected of containing an amphiphilic antigen. Hydrophilic solid supports modified to have hydrophobic surfaces are commercially available, for example, octyl-silica beads (5.0μ diameter, J. T. Baker Co.) and octadecyl-silica beads (3.0μ diameter, Serva). Alternatively, hydrophilic solid supports modified to have a hydrophobic surfaces may be obtained by treating the hydrophilic solid support with a hydrophobic reagent that is capable of generating a hydrophobic surface on the support. When the support and the hydrophobic reagent have opposite charges the generation of the hydrophobic surface will often require only intimate contact of the support with the hydrophobic reagent. Alternatively, either the surface of the support or the hydrophobic reagent will be chemically activated prior to contact, for example, by treatment with a carbodiimide, carbonyldiimidazole, cyanogen bromide, or the like. The treatment may be at room temperature or may require prolonged heating. Hydrophobic reagents capable of generating a hydrophobic surface on the hydrophilic solid support include, but are not limited to, siliconizing agents such as alkylsilanes, alkoxysilanes, alkylhalosilanes, and alkyldisilazanes; alkylation agents such as alkyl alcohols, alkyl halides, alkylamines, and alkylsulfonates; acylation agents such as alkyl esters, isocyanates and fatty acids and their corresponding esters and halides; and antibacterial polypeptides having one or more fatty acid side chains.

In one embodiment of the invention, the hydrophilic solid support is composed of silica, polyacrylamide, sulfonated-polystyrene, or glass, and is preferably in the shape of beads having a diameter of between about 2.0μ and 6.0μ. Most preferred solid supports are octyl-silica and octadecyl-silica beads, octylamine-polyacrylamide beads, glucose oxidase-polymyxin B-sulfonated-polystyrene beads, octylsilane-glass beads.

In another embodiment of the invention the assay medium contains a solubilizing agent. An advantage of employing a solubilizing agent in the assay medium is that the solubilizing agent can be empirically selected in order to prevent the antibody complementary to an amphiphilic antigen from binding to the solid support in the absence of the amphiphilic antigen. For example, chenodeoxycholate prevents antibodies to a lipopolysaccharide from Chlamydia trachomatis from binding to polystyrene microtiter plates unless the lipopolysaccharide is also present in the assay medium. Preferred solubilizing agents of the invention are deoxycholate salts, such as sodium deoxycholate and sodium chenodeoxycholate, alkyl and thialkyl sulfates such as sodium dodecylsulfate and sodium 7-thiatetradecyl sulfate, and alkylglucosides such as octylglucoside. The preparation of thialkyl sulfates as solubilizing agents is disclosed in co-pending U.S. patent application, Ser. No. 07/223,501, filed Jul. 25, 1988, which is herein incorporated in full by reference.

Temperatures employed for solubilizing the amphiphilic antigen are usually in the range from about 10° to 50° C., more usually from about 15° to 100° C. For the most part, relatively short times are required to solubilize an amphiphilic antigen. Usually, the solubilization of an amphiphilic antigen can take at least about 5 seconds and not more than 1 hour, more usually about 30 seconds to about 30 minutes. The time is dependent on the nature of the amphiphilic antigen, and the type and amount of solubilizing agent and temperature used.

The medium containing the solubilizing agent is generally aqueous and may contain up to 40% of an organic solvent. The pH of the medium will usually be in the range of about 2 to 12, more usually in the range of about 5 to 9. The pH is generally chosen to achieve a high level of solubilization of the amphiphilic antigen and subsequently a high level of binding of the amphiphilic antigen to the hydrophobic surface of the solid support. Various buffers may be used to achieve and maintain the pH of this medium. Illustrative buffers include borate, phosphate, carbonate, Tris, barbital and the like. The particular buffer employed is not critical but one buffer may be preferred over another.

After formation of the combination of the hydrophilic solid support modified to have a hydrophobic surface and the assay medium suspected of containing the amphiphilic antigen, the combination is incubated under conditions sufficient for any amphiphilic antigen, if present, to bind to the hydrophobic surface. Usually, the incubation is carried out at a temperature of about 10° to 50° C., preferably 15° to 40° C., at a pH of about 2 to 12, preferably 5 to 9, for a period of about 5 seconds to one hour, preferably about 30 seconds to 30 minutes.

Following incubation of the combination, the presence or amount of amphiphilic antigen bound to the hydrophobic surface is then determined.

In another embodiment, the method of the invention involves the detection of a gram-negative bacterial infection in a patient. In particular, the method involves combining a biological sample from a patient suspected of having a gram-negative bacterial infection with a solubilizing agent of the invention in an amount sufficient to solubilize amphiphilic antigens from the gram-negative bacteria. The resulting combination is then contacted with a hydrophilic solid support modified to have a hydrophobic surface under conditions sufficient for the amphiphilic antigen to bind to the hydrophobic surface. The amount or presence of the amphiphilic antigen bound to the hydrophobic surface is then determined as an indication of a gram-negative bacterial infection in the patient. Preferably, with respect to this embodiment, the amphiphilic antigen is a lipopolysaccharide antigen, and most preferably, a lipopolysaccharide antigen from Chlamydia.

The determination of the presence or amount of amphiphilic antigen bound to the hydrophobic surface can be carried out in a number of ways and examples for purposes of illustration and not limitation follow.

In one embodiment, a hydrophilic solid support modified to have a hydrophobic surface to which the amphiphilic antigen, if any, is bound, is contacted with an antibody for the amphiphilic antigen for a sufficient amount of time to form an antibody-amphiphilic antigen immune complex, which is bound to the hydrophobic surface. The antibody can have a label directly bound to it. Preferably the label is selected from the group consisting of enzymes, coenzymes, fluorescers, chemiluminescers, and radioactive substances. The solid support can then be separated from the assay medium and washed to remove unbound material. The washing solution will generally be aqueous and may contain detergents, substances that enhance or inhibit binding such as polyethylene glycol, chaotropic salts and antichaotropic salts, buffers, e.g., phosphate buffered saline, Tris, borate, and the like. The washing solution can also contain appropriate members of a signal producing system.

In another embodiment wherein the antibody for the amphiphilic antigen is not directly bound to a label, the hydrophobic surface is further contacted with a binding partner for the antibody that has a label directly bound to it. The label, which can be attached covalently or non-covalently to the binding partner, can be any label, preferably an enzyme or coenzyme. Preferably the label is selected from the group consisting of enzymes, coenzymes, fluorescers, chemiluminescers, and radioactive substances. Usually, the binding partner will be included in a separate detection medium but may be included as part of a washing solution or as part of a solution contacted with the hydrophobic surface that contains all the remaining members of the signal producing system that are not bound to the hydrophobic surface. The presence of the label on the hydrophobic surface can then be determined as described herein.

The washing solution and the solutions containing members of the signal producing system will normally consist of aqueous buffered media at a moderate pH, generally that which provides optimum assay sensitivity. The aqueous media may be solely water or may include from 0 to 40 volume percent of a cosolvent. The pH for the medium will usually be in the range of about 4 to 11, more usually in the range of about 5 to 10, and usually will be a compromise between optimum binding of the amphiphilic antigen to the hydrophobic surface of the solid support of the invention and the pH optimum for other reagents of the assay such as members of the signal producing system.

Various buffers may be used to achieve the desired pH and maintain the pH during the determination of the presence or amount of the amphiphilic antigen. Illustrative buffers include borate, phosphate, carbonate, tris, barbital, and the like. The particular buffer employed is not critical to this invention, but in an individual assay one or another buffer may be preferred.

Moderate temperatures are normally employed for carrying out the method of the invention and usually constant temperatures during the period of the assay. Temperatures during the assay may range from about 10° to 50°, more usually from about 15° to 40° C. The temperature selected will be determined by many factors including the nature of the label employed, i.e., enyzmes, fluorescers, chemiluminescers, radioactive substances, and so forth.

The concentration of amphiphilic antigen which may be assayed will generally vary from about $10^{-4}$ to $10^{-15}$M, more usually from about $10^{-6}$ to $10^{-14}$M. Considerations, such as the amount of non-specific binding of label to the hydrophobic surface, the particular detection technique and the concentration of the amphiphilic antigen of intersest will normally determine the concentrations of the various reagents.

While the concentrations of the various reagents in the assay medium will generally be determined by the concentration of the antibody, the final concentration of each of the reagents will normally be determined empirically to optimize the sensitivity of the assay.

After all of the reagents have been combined either simultaneously or sequentially and any immune complex that has been formed has bound to the hydrophobic surface, the level of signal produced by the signal producing system is determined and related to the presence of the amphiphilic antigen. For example, the signal produced with a sample of interest may be compared with the signal produced with a sample that is known to be free of the amphiphilic antigen in order to establish the presence of the amphiphilic antigen in the sample tested. A significantly higher signal produced with the test sample signifies the presence of the amphiphilic antigen.

PREFERRED EMBODIMENTS

Within the various embodiments of the invention, several are preferred.

One preferred embodiment is a method for detecting a lipopolysaccharide antigen in a biological sample suspected of containing the lipopolysaccharide antigen which comprises providing in combination (1) a hydrophilic solid support modified to have a hydrophobic surface by treatment with a hydrophobic reagent selected from the group consisting of an antibacterial polypeptide which has one or more fatty acid side chains of 4 to 12 carbon atoms, an alkylation agent of 4 to 20 carbon atoms, and a siliconizing agent of 1 to 20 carbon atoms; and (2) an assay medium suspected of containing a lipopolysaccharide antigen which contains a solubilizing agent in an amount sufficient to solubilize the lipopolysaccharide antigen; and incubating this combination under conditions sufficient for the lipopolysaccharide antigen to bind to the hydrophobic surface; and then determining the presence or amount of the lipopolysaccharide antigen bound to the hydrophobic surface. Preferably the lipopolysaccharide antigen is from *Chlamydia trachomatis*. Preferably the solubilizing agent is sodium 7-thiatetradecyl sulfate. Preferably the antibacterial polypeptide is polymyxin B or a protein conjugate thereof. Preferably the alkylation agent is an alkylamine, most preferably octylamine or octadecylamine. Preferably the siliconizing agent is an alkylhalosilane, most preferably octyltrichlorosilane or octadecyltrichlorosilane.

In another preferred embodiment, the method of the invention is directed to a method for detecting a lipopolysaccharide antigen in a biological sample suspected of containing the lipopolysaccharide antigen which comprises providing in combination a hydrophilic solid support modified to have a hydrophobic surface and an assay medium suspected of containing a lipopolysaccharide antigen from *Chlamydia trachomatis* which contains sodium 7-thiatetradecyl sulfate in an amount sufficient to solubilize the lipopolysaccharide antigen if present; incubating the combination under conditions sufficient for the lipopolysaccharide antigen to bind to the hydrophobic surface; and determining the presence or amount of the lipopolysaccharide antigen bound to the hydrophobic surface. Preferably the solid support is octylamine-modified-polyacrylamide beads, polymyxin B-modified-sulfonated-polystyrene beads, glucose oxidase-polymyxin B conjugate-modified-sulfonated-polystyrene beads, octyltrichlorosilane-modified-glass beads, and alkyl-silica beads, for example, octyl-silica beads or octadecyl-silica beads.

In another preferred embodiment, the method of the invention is directed to a method of detecting a gram-negative bacterial infection in a patient, which comprises combining a biological sample from a patient suspected of having a gram-negative bacterial infection with a solubilizing agent in an amount sufficient to solubilize an amphiphilic antigen from said gram-negative bacteria; contacting this combination with a hydrophilic solid support modified to have a hydrophobic surface under conditions sufficient for the amphiphilic antigen to bind to the hydrophobic surface; and determining the presence or amount of the amphiphilic antigen bound to the hydrophobic surface as an indication of a gram-negative bacterial infection in the patient. Preferably the amphiphilic antigen is a lipopolysaccharide antigen from *Chlamydia trachomatis*.

The following preparations and examples are given to enable those skilled in the art to more clearly understand and to practice the instant invention. They should not be considered as a limitation on the scope of the invention, but merely as being illustrative and representative thereof.

PREPARATION 1

Conjugation of Polymyxin B and Protein

A. Horseradish peroxidase (HRP) (5.0 mg/mL) in sodium acetate buffer (10 mM sodium acetate, pH 4.5) was passed over a PD10 column (Pharmacia premade G25 column). A 1.0 mL aliquot of the HRP solution was cooled to 0° C. Sodium periodate (0.2 mL, 0.1M) was then added very slowly to the HRP aliquot while vortexing. The resulting solution was then cooled to 0° and incubated for 30 minutes without stirring. The solution was then passed down a PD10 column in sodium acetate buffer. The purified HRP (1.0 mL) was then added to 1.0 mL of polymyxin B (80 mg) in phosphate-buffered saline (PBS) (100 mM sodium phosphate, 200 mM sodium chloride, pH 7.0), while stirring. The reaction mixture was incubated for 24 hours in the dark at room temperature without stirring. To the reaction mixture was then added 0.3 mL of borate buffer (4.0 mg/mL sodium borohydride in $H_2O$) while stirring. The resulting mixture was incubated for 2 hours at 0° C. The mixture was then passed down a Sephadex G25 column in PBS to yield HRP-polymyxin B conjugate.

B. In a similar manner, but replacing horseradish peroxidase with glucose oxidase, glucose oxidase-polymyxin B conjugate was prepared.

PREPARATION 2

Preparation of Hydrophobic Surfaces

A. Preparation of Polymyxin B-Polystyrene Beads

Sulfonated-polystyrene beads (2.17μ, IDC) were washed extensively with water and drained. A 10% suspension of the beads in glycine buffer was made. The suspension (45 μl) was then added to 450 μL of polymyxin B (2.0 mg/mL in PBS). The suspension was then sonicated for 1 minute and then placed on a rocking platform for 2 hours, with sonication for 1 minute at 1 hour and 2 hours. The beads were then filtered out of the suspension and washed with glycine buffer. The beads were then resuspended in 500 μL of glycine buffer (10 mM glycine, 10 mM sodium chloride, 0.005% thimerosal, 0.02% sodium azide, pH 8.2) to give a 1.0% suspension of polymyxin B-sulfonated-polystyrene beads.

B. Preparation of Glucose Oxidase-Polymyxin B Conjugate-Polystyrene Beads

In a similar manner, sulfonated-polystyrene beads (2.17μ, $SO_4$) were treated with glucose oxidase-polymyxin B conjugated (0.46 mg/mL in PBS) (as prepared in Preparation 1 above) to yield glucose oxidase-polymyxin B conjugate-sulfonated-polystyrene beads (1.0% suspension).

C. Preparation of Octylamine-Polyacrylamide Beads

Polyacrylamide beads (3.0 ml, 3.0μ, BioRad, Lot #170-5910) were washed twice with 3.0 mL borate buffer (0.25M sodium borohydride, pH 9.4), then twice with 4-morpholineethanesulfonic acid (10 mM, pH 6.3) (MES). The beads were then suspended in 3.0 mL MES. To this suspension was added 1-ethyl-3-(3-dimethylaminopropyl) carbodiimide (EDAC) (40 mg). The suspension was vortexed for 3 minutes. The the suspension was then added 3.0 mL of octylamine (0.1% in MES, 10 mM, pH 6.3). The suspension was stirred overnight at room temperature. The suspension was then washed three times with 5.0 mL glycine buffer (0.17M glycine, 0.1 NaCl, pH 9.2) to afford octylamine-polyacrylamide beads.

D. Preparation of Octyltrichloro-Silane-Glass Beads

Glass beads (1.0 to 5.0μ diameter, Polyscience, Lot #23310) were washed twice with water and then twice with MES (10 mM, pH 6.3). The beads were then resuspended in 8.0 mL of water (50 mg/mL). 2.0 mL of the suspension was then washed twice with 5.0 mL methanol, twice with 5.0 mL acetone and then once with 5.0 mL methylene chloride. To the pellet of beads was then added a 1.0 mL solution of octyltrichloro silane in methylene chloride (0.25 mL of octyltrichloro silane diluted 1:1000 with methylene chloride, 0.75 mL of methylene chloride). The resulting suspension was then incubated for 20 minutes at room temperature. The beads were then washed twice with 3.0 mL acetone, then twice with 3.0 mL methanol, then twice with 3.0 mL water. The beads were resuspended in 1.0 methanol to afford octyltrichlorosilane-glass beads.

PREPARATION 3

Preparation of Glucose Oxidase-Beads

The following preparation was performed at 4° C. 2.0 mL of a glucose oxidase solution (7.23 mg/mL, Biozyme) was diluted to 21.0 mL with saline solution (0.1M sodium chloride). This solution was dialyzed overnight against 1.0 L of saline. To a solution of carboxylated-polystyrene beads (0.88μ) in water (28.0 mL, 1.875% w/v) 1-ethyl-3-(3-dimethylaminopropyl) carbodiimide (EDAC) (262.5 mg) was added while vortexing. The resulting suspension was incubated for 4 minutes while stirring continuously. The suspension was then added to the glucose oxidase solution previously prepared. The resulting suspension was incubated overnight on a rotator. The beads within the suspension were then collected by centrifugation (10,000 rpm for 10 minutes) and then resuspended in 35.0 mL of glycine buffer (0.17M glycine, 0.1 sodium chloride, 0.005% thimerosal, pH 9.2). The beads were then collected two more times by centrifugation and resuspended each time in 35.0 mL of the glycine buffer (with 1.0% bovine serum albumin added). The beads were then incubated in the glycine-BSA buffer for 2 hours on a rotator. The beads were then collected three more times by centrifugation and each time resuspended in 35.0 mL Tris buffer (0.2M Tris/HCl, pH 7.5) to afford glucose oxidase-beads.

PREPARATION 4

Preparation of a Solubilizing Agent of the Invention

A. A solution of heptyl mercaptan (13.23 g, 0.105 mol) in tetrahydrofuran (THF) was added to a vigorously stirred suspension of sodium hydride (2.6 g, 0.105 mol) in THF (170 mL) over 45 minutes. The mixture was stirred under argon at room temperature for one hour. Chlorohexanol (13.44 g, 0.1 mol) in THF was added to the vigorously stirred mixture over a period of 30-45 minutes. The mixture was then stirred under argon at room temperature for 24 hours. Reaction completion was then checked by thin layer chromatography. The THF was then evaporated on a rotary evaporator. Water was then added to the mixture, and extraction was performed three times with ethyl acetate (EtOAc). The EtOAc extraction was washed with water. Then the EtOAc extracts were washed with saturated brine, and dried over $Na_2SO_4$. The $Na_2SO_4$ was filtered and evaporated to a yellow oil on a rotary evaporator. The product was then chromatographed with a Waters Prep 500 HPLC, using hexane-EtOAc. Appropriate fractions were combined and evaporated to a clear, light yellow oil. The oil was then distilled under vacuum, boiling point 85°-100° C./0.01 mm. to yield 7-thiatetradecan-1-ol (19.09 g, 82% yield).

B. Ethyl ether ($Et_2O$) (100 mL) was cooled to 0°-5° C. with stirring under argon. $ClSO_3H$ (10.04 g, 0.086 mol) was then added dropwise to the $Et_2O$, maintaining temperature at 0°-5° C. 7-thiatetradecan-1-ol (19.09 g, 0.082 mol), as prepared in Section A above, was then added dropwise to the mixture, maintaining temperature at 0°-5° C. The $Et_2O$ was then removed on rotary evaporator; $Et_2O$ was then added to the mixture and evaporated again on a rotary evaporator/vacuum pump. The resulting solution was poured slowly into an NaOH/ice solution. The pH was adjusted to 10. An extraction was then made with petroleum ether. Ethanol was added to assist in phase separation and defoaming. The product was dried by rotary evaporation followed by lyophilization to yield sodium 7-thiatetradecyl sulfate (26.18 g, 95% yield).

PREPARATION 5

The formulations of the solutions used in the following Examples are as follows:
A. Sample Solubilization Buffer Solution:
0.1% sodium 7-thiatetradecyl sulfate, 6.5M dithiothreitol, 10 mM ethylenediaminetetraacetic acid (EDTA) in phosphate-buffered saline, pH 7.4
B. Silica Beads Solution:
5.0% (w.v) of alkyl-silica beads in 0.2% octyl-glucoside and 0.1% bovine serum albumin in phosphate-buffered saline, pH 7.4. Alkyl silica beads include octyl-silica beads (5.0μ diameter) from J. T. Baker Co., Lot #1334106, octadecyl-silica beads (3.0μ diameter) from Serva, Lot #43546.
C. Antibody Solution:
Affinity purified rabbit polyclonal antisera raised specifically against *Chlamydia trachomatis* in 0.1% chenodeoxycholate, 1.0% dextran in 0.2M tris, pH 7.2.
D. Binding Partner Solution:
Horseradish peroxidase-goat anti-rabbit IgG conjugate, 1.0% fish gelatin, 1.0% diethylaminoethyl-dextran (Pharmacia), 0.2 mg/mL 8-anilino-1-naphthalenesulfonic acid, 0.1 trypsin inhibiting units, and 0.01% thimerosal in phosphate-buffered saline (25 mM sodium phosphate, 150 mM sodium chloride, pH 6.6).
E. Blocking Solution:
50% Moducyte (IV) (Miles), 0.1% Tween 20, and 0.5% octyl-glucoside in Tris-buffered saline, pH 7.5.

EXAMPLE 1

A. Stock Chlamydia elementary bodies (formaldehyde (0.1%) fixed at $10^{10}$ IFU/mL) were placed in sample solubilization buffer (as prepared in Preparation 5, Section A, above). 50 μL of this solution was then combined with 35 μL of octyl-silica bead solution (as prepared in Preparation 5, Section B, above) and 15 μL of glucose oxidase-polystyrene beads (as prepared in Preparation 3, above) to form an assay solution. The assay solution was then placed in a test well containing a glass fiber filter on top of an absorbent pad. The binding reaction was stopped by the addition to the test well of 100 μL of blocking solution (as prepared in Preparation 5, section E, above). 50 μL of antibody solution (as prepared in Preparation 5, section C, above) was then added to the test well and allowed to incubate at room temperature for 5 minutes. The binding reaction was then stopped by the addition to the test well of 100 μL of blocking solution. 50 μL of binding partner solution (as prepared in Preparation 5, section D, above) was then added to the test well and allowed to incubate for 5 minutes at room temperature. The binding reaction was then stopped by the addition to the test well of 50 μL of blocking solution, followed by the addition of citrate (100 μL). 50 μL of a substrate solution was then added to the test well and the resulting color read at 5 and 10 minutes. The reaction was stopped with the addition of 100 μL citrate to the test well. This assay effectively detected the presence of amphiphilic antigen from Chlamydia bound to the hydrophobic surface of the octyl-silica beads.

B. In a similar manner, but replacing octyl-silica beads with octadecyl-silica beads, the assay effectively detected the presence of amphiphilic antigen from Chlamydia bound to the hydrophobic surface of the octadecyl-silica beads.

C. In a similar manner, but replacing octadecyl-silica beads with octylamine-polyacrylamide beads (as prepared in Preparation 2, Section C, above), the assay effectively detected the presence of amphiphilic antigen from Chlamydia bound to the hydrophobic surface of the octylamine-polyacrylamide beads.

D. In a similar manner, but replacing octylamine-polyacrylamide beads with octyltrichlorosilane-glass beads (as prepared in Preparation 2, Section D, above), the assay effectively detected the presence of amphiphilic antigen from Chlamydia bound to the hydrophobic surface of the octyltrichlorosilane-glass beads.

EXAMPLE 2

Clinical Study

A clinical sample suspected of containing Chlamydia was collected on a swab. The swab was then placed in 0.5 mL of sample solubilization buffer solution (as prepared in Preparation 5, Section A, above) for 15 minutes at room temperature and then vortexed. The swab was then removed from the solution and the solution was then filtered. 50 μL of the solution was then combined with 35 μl of octadecyl-silica bead solution (as prepared in Preparation 5, Section B, above) and 15 μl of glucose oxidase-polystyrene beads to form an assay solution. The assay solution was then placed in a test well containing a glass fiber filter on top of an absorbent pad. The binding reaction was stopped by the addition to the test well of 100 μL of blocking solution (as prepared in Preparation 5, Section E, above). 50 μL of antibody solution (as prepared in Preparation 5, Section C, above) was then added to the test well and allowed to incubate at room temperature for 5 minutes. The binding reaction was then stopped by the addition to the test well of 100 μL of blocking solution. 50 μL of binding partner solution (as prepared in Preparation 5, section D, above) was then added to the test well and allowed to incubate for 5 minutes at room temperature. The binding reaction was then stopped by the addition to the test well of 50 μL of blocking solution, followed by the addition of citrate (100 μL). 50 μL of a substrate solution was then added to the test well and the resulting color read at 5 and 10 minutes. The reaction was stopped with addition to the test well of 100 μL citrate. This assay effectively determined the presence of amphiphilic antigens from Chlamydia bound to the hydrophobic surface of the solid support as an indication of the presence of Chlamydia in the clinical sample.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for detecting an amphiphilic antigen in a biological sample suspected of containing said antigen which comprises:
    (a) providing in combination:
        (i) a hydrophilic solid support modified to have a hydrophobic surface by treatment with a hydrophobic reagent that is capable of generating a hydrophobic surface on said solid support, said hydrophobic reagent being selected from the group consisting of antibacterial polypeptides having one or more fatty acid side chains of 4 to 12 carbon atoms, siliconizing agents of 4 to 20 carbon atoms, alkylation agents of 4 to 20 carbon atoms, and acylation agents of 4 to 20 carbon atoms; and
        (ii) an assay medium suspected of containing an amphiphilic antigen;
    (b) incubating said combination under conditions sufficient for said amphiphilic antigen to bind to said hydrophobic surface; and
    (c) determining the presence or amount of said amphiphilic antigen bound to said hydrophobic surface, wherein said determining comprises contacting said hydrophobic surface with an antibody specific for said amphiphilic antigen to form an antibody-amphiphilic antigen immune complex bound to said hydrophobic surface.

2. A method of claim 1 where said amphiphilic antigen is a lipopolysaccharide antigen from a gram-negative bacterium.

3. A method of claim 2 where said gram-negative bacterium is selected from the group consisting of *Chlamydia trachomatis*, *Chlamydia psittaci*, and *Neisseria gonorrhoeae*.

4. A method of claim 1 where said hydrophilic solid support is composed of silica, polyacrylamide, glass, sulfonated-polystyrene, or carboxylated-polystyrene.

5. A method of claim 1 where said antibacterial polypeptide is polymyxin B or a protein-polymyxin B conjugate.

6. A method of claim 1 where said siliconizing agent is selected from the group consisting of alkylsilanes, alkoxysilanes, alkylhalosilanes, and alkyldisilazanes.

7. A method of claim 6 where said siliconizing agent is octyltrichlorosilane.

8. A method of claim 1 where said siliconizing agent is octadecyltrichlorosilane.

9. A method of claim 1 where said alkylation agent is selected from the group consisting of alkyl alcohols, alkyl halides, alkyl sulfonates, and alkylamines.

10. A method of claim 9 where said alkylation agent is octylamine.

11. A method of claim 1 where said acylation agent is selected from the group consisting of fatty acids and their corresponding esters and halides, alkyl sulfonyl halides, and alkyl isocyanates.

12. A method of claim 1 where said assay medium contains a solubilizing agent.

13. A method of claim 12 where said solubilizing agent is selected from the group consisting of an alkyl sulfate of 8 to 20 carbons, a thialkyl sulfate of 8 to 20 carbons, and a deoxycholate salt.

14. A method of claim 13 where said solubilizing agent is sodium 7-thiatetradecyl sulfate.

15. A method of claim 1 where said antibody has a label bound to it.

16. A method of claim 15 where said label is selected from the group consisting of enzymes, coenzymes, fluorescers, chemiluminescers, and radioactive substances.

17. A method of claim 1 which further comprises contacting said hydrophobic surface with a binding partner for said antibody that has a label bound to it.

18. A method of claim 17 where said label is selected from the group consisting of enzymes, coenzymes, fluorescers, chemiluminescers, and radioactive substances.

19. A method for detecting a lipopolysaccharide antigen in a biological sample suspected of containing said lipopolysaccharide antigen which comprises:
 (a) providing in combination
  (1) a hydrophilic solid support modified to have a hydrophobic surface by treatment with an antibacterial polypeptide having one or more fatty acid side chains of 4 to 12 carbon atoms, which is capable of generating a hydrophobic surface on said hydrophilic solid support; and
  (2) an assay medium suspected of containing a lipopolysaccharide antigen which contains a solubilizing agent in an amount sufficient to solubilize said lipopolysaccharide antigen;
 (b) incubating said combination under conditions sufficient for said lipopolysaccharide antigen to bind to said hydrophobic surface; and
 (c) determining the presence or amount of said lipopolysaccharide antigen bound to said hydrophobic surface, wherein said determining comprises contacting said hydrophobic surface with an antibody specific for said lipopolysaccharide antigen to form an antibody-lipopolysaccharide antigen immune complex bound to said hydrophobic surface.

20. A method of claim 19 where said antibacterial polypeptide is polymyxin B.

21. A method of claim 19 where said lipopolysaccharide antigen is from *Chlamydia trachomatis*.

22. A method of claim 19 where said solubilizing agent is sodium 7-thiatetradecyl sulfate.

23. A method for detecting a lipopolysaccharide antigen in a biological sample suspected of containing said lipopolysaccharide antigen which comprises:
 (a) providing in combination
  (1) a hydrophilic solid support modified to have a hydrophobic surface by treatment with an alkylation agent of 4 to 20 carbon atoms capable of generating a hydrophobic surface on said hydrophilic solid support; and
  (2) an assay medium suspected of containing a lipopolysaccharide antigen which contains a solubilizing agent in an amount sufficient to solubilize said lipopolysaccharide antigen;
 (b) incubating said combination under conditions sufficient for said lipopolysaccharide antigen to bind to said hydrophobic surface; and
 (c) determining the presence or amount of said lipopolysaccharide antigen bound to said hydrophobic surface, wherein said determining comprises contacting said hydrophobic surface with an antibody specific for said lipopolysaccharide antigen to form an antibody-lipopolysaccharide antigen immune complex bound to said hydrophobic surface.

24. A method of claim 23 where said alkylation agent is octylamine or octadecylamine.

25. A method of claim 23 where said lipopolysaccharide antigen is from *Chlamydia trachomatis*.

26. A method of claim 23 where said solubilizing agent is sodium 7-thiatetradecyl sulfate.

27. A method for detecting a lipopolysaccharide antigen in a biological sample suspected of containing said lipopolysaccharide antigen which comprises:
 (a) providing in combination
  (1) a hydrophilic solid support modified to have a hydrophobic surface by treatment with a siliconizing agent of 1 to 20 carbon atoms capable of generating a hydrophobic surface on said hydrophilic solid support; and
  (2) an assay medium suspected of containing a lipopolysaccharide antigen which contains a solubilizing agent in an amount sufficient to solubilize said lipopolysaccharide antigen;
 (b) incubating said combination under conditions sufficient for said lipopolysaccharide antigen to bind to said hydrophobic surface; and
 (c) determining the presence or amount of said lipopolysaccharide antigen bound to said hydrophobic surface, wherein said determining comprises contacting said hydrophobic surface with an antibody specific for said lipopolysaccharide antigen to form an antibody-lipopolysaccharide antigen immune complex bound to said hydrophobic surface.

28. A method of claim 27 where said siliconizing agent is an alkylhalosilane.

29. A method of claim 28 where said alkylhalosilane is octyltrichlorosilane or octadecyltrichlorosilane.

30. A method of claim 27 where said lipopolysaccharide antigen is from *Chlamydia trachomatis*.

31. A method of claim 27 where said solubilizing agent is sodium 7-thiatetradecyl sulfate.

32. A method for detecting a lipopolysaccharide antigen in a biological sample suspected of containing said lipopolysaccharide antigen which comprises:
 (a) providing in combination:
  (i) a hydrophilic solid support modified to have a hydrophobic surface by treatment with a hydrophobic reagent that is capable of generating a hydrophobic surface on said solid support, said hydrophobic reagent being selected from the group consisting of antibacterial polypeptides having one or more fatty acid side chains of 4 to 12 carbon atoms, siliconizing agents of 4 to 20 carbon atoms, alkylation agents of 4 to 20 carbon atoms, and acylation agents of 4 to 20 carbon atoms; and (ii) an assay medium suspected of containing a lipopolysaccharide antigen from *Chlamydia trachomatis* which contains sodium 7-thiatetradecyl sulfate in an amount sufficient to solubilize said lipopolysaccharide antigen;

(b) incubating said combination under conditions sufficient for said lipopolysaccharide antigen to bind to said hydrophobic surface; and (c) determining the presence or amount of said lipopolysaccharide antigen bound to said hydrophobic surface, wherein said determining comprises contacting said hydrophobic surface with an antibody specific for said lipopolysaccharide antigen to form an antibody-lipopolysaccharide antigen immune complex bound to said hydrophobic surface.

33. A method of claim 32 where said solid support is alkyl-silica beads.

34. A method of claim 33 where said solid support is octyl-silica beads.

35. A method of claim 33 where said solid support is octadecyl-silica beads.

36. A method of claim 33 where said solid support is octylamine-polyacrylamide beads.

37. A method of claim 33 where said solid support is polymyxin B-sulfonated-polystyrene beads.

38. A method of claim 33 where said solid support is glucose oxidase-polymyxin B conjugate-sulfonated-polystyrene beads.

39. A method of claim 33 where said solid support is octyltrichlorosilane-glass beads.

40. A method of detecting a gram-negative bacterial infection in a patient, which comprises:

(a) combining a biological sample from a patient suspected of having a gram-negative bacterial infection with a solubilizing agent in an amount sufficient to solubilize an amphiphilic antigen from said gram-negative bacteria;

(b) contacting said combination with a hydrophilic solid support modified to have a hydrophobic surface under conditions sufficient for said amphiphilic antigen to bind to said hydrophobic surface, wherein said hydrophilic solid support is treated with a hydrophobic reagent that is capable of generating a hydrophobic surface on said solid support, said hydrophobic reagent being selected from the group consisting of antibacterial polypeptides having one or more fatty acid side chains of 4 to 12 carbon atoms, siliconizing agents of 4 to 20 carbon atoms alkylation agents of 4 to 20 carbon atoms, and acylation agents of 4 to 20 carbon atoms; and (c) determining the presence or amount of said amphiphilic antigen bound to said hydrophobic surface as an indication of a gram-negative bacterial infection in said patient, wherein said determining comprises contacting said hydrophobic surface with an antibody specific for said lipopolysaccharide antigen to form an antibody-lipopolysaccharide antigen immune complex bound to said hydrophobic surface.

41. A method of claim 40 where said amphiphilic antigen is a lipopolysaccharide antigen from Chlamydia.

* * * * *